(12) United States Patent
Gorzitze

(10) Patent No.: US 12,714,390 B2
(45) Date of Patent: Aug. 25, 2026

(54) NEEDLE GUIDES FOR A SONOGRAPHIC IMAGING DEVICE

(71) Applicant: C. R. Bard, Inc., Franklin Lakes, NJ (US)

(72) Inventor: Jonathan C. Gorzitze, Kaysville, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 19/207,179

(22) Filed: May 13, 2025

(65) Prior Publication Data

US 2025/0268562 A1 Aug. 28, 2025

Related U.S. Application Data

(60) Division of application No. 16/356,800, filed on Mar. 18, 2019, now abandoned, which is a continuation of (Continued)

(51) Int. Cl.
*A61B 8/08* (2006.01)
*A61B 17/34* (2006.01)
(Continued)

(52) U.S. Cl.
CPC .......... *A61B 8/0841* (2013.01); *A61B 8/0833* (2013.01); *A61B 17/3403* (2013.01); *A61M 5/3287* (2013.01); *A61M 5/427* (2013.01); *A61B 2017/3411* (2013.01); *A61B 2017/3413* (2013.01)

(58) Field of Classification Search
CPC ....... A61B 17/3403; A61B 2017/3411; A61M 5/3287
See application file for complete search history.

(56) References Cited

U.S. PATENT DOCUMENTS 2,470,488 A 5/1949 Honerkamp et al.
4,058,114 A 11/1977 Soldner
(Continued)

FOREIGN PATENT DOCUMENTS

CN 3655315 6/2007
DE 2942405 A1 4/1981
(Continued)

OTHER PUBLICATIONS

U.S. Appl. No. 14/581,019, filed Dec. 23, 2014 Final Office Action dated Aug. 7, 2018.

(Continued)

*Primary Examiner* — Boniface N Nganga
(74) *Attorney, Agent, or Firm* — Rutan & Tucker LLP

(57) ABSTRACT

A medical device guide system includes a probe configured for imaging portions of a patient's body, a first guide connector extending from a first surface of the probe, the first guide connector including a first mounting surface, and a guide removably mountable to the first guide connector. The guide may include a first cavity shaped to receive the first mounting surface and a first channel disposed on a top surface of the guide opposite the first cavity, the first channel angled at a first angle with respect to a longitudinal axis of the probe and configured to guide a medical device to a targeted depth in the patient's body.

19 Claims, 14 Drawing Sheets

Related U.S. Application Data application No. 13/886,196, filed on May 2, 2013, now Pat. No. 10,231,697, which is a division of application No. 12/642,456, filed on Dec. 18, 2009, now Pat. No. 8,574,160.

(60) Provisional application No. 61/138,606, filed on Dec. 18, 2008.

(51) Int. Cl.
*A61M 5/32* (2006.01)
*A61M 5/42* (2006.01)

(56) References Cited

U.S. PATENT DOCUMENTS 4,108,165 A 8/1978 Kopp et al.
4,341,303 A 7/1982 Britt
4,346,717 A 8/1982 Haerten
4,363,326 A 12/1982 Kopel
4,402,324 A 9/1983 Lindgren et al.
4,408,611 A 10/1983 Enjoji
4,469,106 A 9/1984 Harui
4,497,325 A 2/1985 Wedel
4,548,210 A 10/1985 Enjoji et al.
4,576,175 A 3/1986 Epstein
4,582,326 A 4/1986 Alsip
4,608,989 A 9/1986 Drue
4,635,644 A 1/1987 Yagata
4,662,870 A 5/1987 Augustine et al.
4,681,103 A 7/1987 Boner et al.
4,723,544 A 2/1988 Moore et al.
4,742,829 A 5/1988 Law et al.
4,838,506 A 6/1989 Cooper
4,877,033 A 10/1989 Seitz, Jr.
4,883,059 A 11/1989 Stedman et al.
4,898,178 A 2/1990 Wedel
4,899,756 A 2/1990 Sonek
4,911,173 A 3/1990 Terwilliger
5,052,396 A 10/1991 Wedel et al.
5,076,279 A 12/1991 Arenson et al.
5,100,387 A 3/1992 Ng
5,138,748 A 8/1992 Welles
5,235,987 A 8/1993 Wolfe
5,265,614 A 11/1993 Hayakawa et al.
5,280,427 A 1/1994 Magnusson et al.
5,427,108 A 6/1995 Bollinger
D362,064 S 9/1995 Smick
5,494,039 A 2/1996 Onik et al.
5,623,931 A 4/1997 Wung et al.
5,758,650 A 6/1998 Miller et al.
D399,971 S 10/1998 Scherer
5,911,707 A 6/1999 Wolvek et al.
D412,032 S 7/1999 Mikula-Curtis et al.
5,924,992 A 7/1999 Park et al.
5,941,889 A 8/1999 Cermak
6,050,954 A 4/2000 Mittermeier
D424,693 S 5/2000 Pruter
6,083,169 A 7/2000 Hansen
6,095,981 A 8/2000 McGahan
D434,850 S 12/2000 Balestracci
6,203,499 B1 3/2001 Imling et al.
6,283,942 B1 9/2001 Staehlin et al.
6,296,614 B1 10/2001 Pruter
6,361,499 B1 3/2002 Bates et al.
6,368,280 B1 4/2002 Cermak et al.
6,379,307 B1 4/2002 Filly et al.
6,425,871 B1 7/2002 Jaggi
6,475,152 B1 11/2002 Kelly, Jr. et al.
6,485,426 B2 11/2002 Sandhu
6,612,990 B1 9/2003 Pruter
6,695,786 B2 2/2004 Wang et al.
6,743,177 B2 6/2004 Ito
6,758,817 B1 7/2004 Pruter et al.
6,814,704 B2 11/2004 Weilandt
6,840,954 B2 1/2005 Dietz et al.
6,877,352 B1 4/2005 Schlereth
6,884,219 B1 4/2005 Pruter
6,908,433 B1 6/2005 Pruter
7,022,082 B2 4/2006 Sonek
7,087,024 B1 8/2006 Pruter
7,322,990 B1 1/2008 Mark et al.
7,351,205 B2 4/2008 Szczech et al.
7,452,331 B1 11/2008 Pruter
7,588,541 B2 9/2009 Floyd et al.
7,635,336 B1 12/2009 Pruter
7,670,294 B2 3/2010 Kisen et al.
7,691,066 B2 4/2010 Kosaku
D625,802 S 10/2010 Choi et al.
D625,805 S 10/2010 Hereford
7,837,627 B1 11/2010 Pruter
D629,898 S 12/2010 Bigelow
D630,731 S 1/2011 Schmutzer et al.
7,909,815 B2 3/2011 Whitmore, III et al.
7,976,469 B2 7/2011 Bonde et al.
D649,245 S 11/2011 Klebs et al.
8,073,529 B2 12/2011 Cermak et al.
8,075,495 B2 12/2011 Andreyko et al.
8,118,743 B2 2/2012 Park et al.
D655,813 S 3/2012 Row et al.
8,137,281 B2 3/2012 Huang et al.
D659,825 S 5/2012 Dillard, III
D672,460 S 12/2012 Baid
8,430,889 B2 4/2013 Zeng et al.
D683,019 S 5/2013 Shahidi Bonjar
8,496,593 B2 7/2013 Park et al.
8,523,824 B2 9/2013 Teirstein et al.
8,574,160 B2 11/2013 Gorzitze
8,641,620 B2 2/2014 Lasser et al.
8,647,280 B2 2/2014 Ooishi et al.
8,696,583 B2 4/2014 Ohgishi et al.
8,696,585 B2 4/2014 Addison et al.
8,708,916 B2 4/2014 Okuno
8,740,800 B2 6/2014 Wakabayashi et al.
8,747,324 B1 6/2014 Pruter et al.
D710,995 S 8/2014 Shirley et al.
8,795,183 B2 8/2014 Siebrecht et al.
8,808,186 B2 8/2014 Fruland et al.
D727,495 S 4/2015 Bown et al.
D752,743 S 3/2016 Oberg et al.
9,788,812 B2 10/2017 Orome et al.
9,974,516 B2 5/2018 Orome et al.
10,231,697 B2 3/2019 Gorzitze
10,524,691 B2 1/2020 Newman et al.
10,863,970 B2 12/2020 Oberg et al.
2002/0123689 A1 9/2002 Furia
2002/0133079 A1 9/2002 Sandhu
2003/0144627 A1 7/2003 Woehr et al.
2003/0195425 A1 10/2003 Ito
2004/0133111 A1 7/2004 Szczech et al.
2005/0059891 A1 3/2005 Kosaku
2005/0113816 A1 5/2005 Whitmore et al.
2005/0143753 A1 6/2005 Whitmore et al.
2005/0267373 A1 12/2005 Lee
2006/0129046 A1 6/2006 Stevens et al.
2006/0150876 A1 7/2006 Green et al.
2006/0241477 A1 10/2006 Sasady et al.
2007/0016781 A1 1/2007 Asokan et al.
2007/0038113 A1 2/2007 Oonuki et al.
2007/0073155 A1 3/2007 Park et al.
2007/0078346 A1 4/2007 Park et al.
2007/0112272 A1 5/2007 Park et al.
2007/0167817 A1 7/2007 Huang et al.
2007/0276241 A1 11/2007 Park et al.
2007/0276253 A1 11/2007 Park et al.
2007/0282205 A1 12/2007 Furia
2008/0033454 A1 2/2008 Lukoschek et al.
2008/0300491 A1 12/2008 Bonde et al.
2009/0143684 A1 6/2009 Cermak et al.
2009/0171219 A1 7/2009 Uchibori
2009/0247876 A1 10/2009 Cannon, Jr. et al.
2009/0266957 A1 10/2009 Cermak
2009/0270722 A1 10/2009 Floyd et al.
2009/0275833 A1 11/2009 Ikeda et al.

(56) References Cited

U.S. PATENT DOCUMENTS

| | | | |
|---|---|---|---|
| 2010/0010475 | A1 | 1/2010 | Teirstein et al. |
| 2010/0041990 | A1 | 2/2010 | Schlitt et al. |
| 2010/0081920 | A1 | 4/2010 | Whitmore, III et al. |
| 2010/0106056 | A1 | 4/2010 | Norris |
| 2010/0160787 | A1 | 6/2010 | Gorzitze |
| 2010/0228131 | A1 | 9/2010 | Oonuki et al. |
| 2010/0247513 | A1 | 9/2010 | Agee et al. |
| 2010/0312121 | A1 | 12/2010 | Guan |
| 2011/0028847 | A1 | 2/2011 | Whitmore, III et al. |
| 2012/0165679 | A1 | 6/2012 | Orome et al. |
| 2012/0330159 | A1 | 12/2012 | Orome et al. |
| 2013/0150714 | A1 | 6/2013 | Howlett et al. |
| 2013/0245452 | A1 | 9/2013 | Gorzitze |
| 2015/0025315 | A1 | 1/2015 | Nishina et al. |
| 2015/0112200 | A1 | 4/2015 | Oberg et al. |
| 2019/0209120 | A1 | 7/2019 | Gorzitze |

FOREIGN PATENT DOCUMENTS

| | | | |
|---|---|---|---|
| EP | 1709919 | A1 | 10/2006 |
| JP | 01097440 | A | 4/1989 |
| JP | 03173542 | A | 7/1991 |
| JP | 11128237 | A | 5/1999 |
| JP | 21161683 | | 6/2001 |
| JP | 21340334 | | 12/2001 |
| JP | 23299654 | | 10/2003 |
| JP | 23334191 | | 11/2003 |
| JP | 2005034273 | A | 2/2005 |
| JP | D1268564 | | 4/2006 |
| JP | 2009153831 | A | 7/2009 |
| JP | 2010115246 | A | 5/2010 |
| WO | 1996010958 | A2 | 4/1996 |
| WO | 2000019906 | A1 | 4/2000 |
| WO | 2000040155 | A1 | 7/2000 |
| WO | 2003094701 | A2 | 11/2003 |
| WO | 2004021898 | A1 | 3/2004 |
| WO | 2006060657 | A2 | 6/2006 |
| WO | 2007027511 | A2 | 3/2007 |
| WO | 2007040172 | A1 | 4/2007 |
| WO | 2007110076 | A1 | 10/2007 |
| WO | 2008024515 | A2 | 2/2008 |
| WO | 2009073653 | A1 | 6/2009 |
| WO | 2009090230 | A1 | 7/2009 |
| WO | 2010080637 | A1 | 7/2010 |
| WO | 2010084322 | A1 | 7/2010 |
| WO | 2012088458 | | 6/2012 |
| WO | 2012178109 | | 12/2012 |
| WO | 2013054168 | A2 | 4/2013 |
| WO | 2015100332 | A1 | 7/2015 |

OTHER PUBLICATIONS

U.S. Appl. No. 14/581,019, filed Dec. 23, 2014 Final Office Action dated Feb. 3, 2020.
U.S. Appl. No. 14/581,019, filed Dec. 23, 2014 Non-Final Office Action dated Apr. 12, 2017.
U.S. Appl. No. 14/581,019, filed Dec. 23, 2014 Non-Final Office Action dated Oct. 7, 2019.
U.S. Appl. No. 16/356,800, filed Mar. 18, 2019 Board Decision dated Jan. 8, 2025.
U.S. Appl. No. 16/356,800, filed Mar. 18, 2019 Examiner's Answer dated Jan. 12, 2023.
U.S. Appl. No. 16/356,800, filed Mar. 18, 2019 Final Office Action dated May 9, 2022.
U.S. Appl. No. 16/356,800, filed Mar. 18, 2019 Non-Final Office Action dated Jan. 27, 2022.
U.S. Appl. No. 17/121,742, filed Dec. 14, 2020 Notice of Allowance dated Sep. 1, 2022.
U.S. Appl. No. 29/493,150, filed Jun. 5, 2014 Notice of Allowance dated Oct. 29, 2015.
CN 201180067467.2 filed Aug. 13, 2013 First Office Action dated Sep. 4, 2014.
CN 201180067467.2 filed Aug. 13, 2013 second Office Action dated Apr. 30, 2015.
CN 201180067467.2 filed Aug. 13, 2013 Third Office Action dated Oct. 28, 2015.
CN 201280030885.9 filed Dec. 23, 2013 First Office Action dated Mar. 3, 2015.
CN 201280030885.9 filed Dec. 23, 2013 Second Office Action dated Nov. 4, 2015.
CN 201280030885.9 filed Dec. 23, 2013 Third Office Action dated May 5, 2016.
CN 201480070757.6 filed Jun. 23, 2016 Office Action dated Aug. 31, 2018.
CN 201480070757.6 filed Jun. 23, 2016 Office Action dated May 17, 2019.
CN 201480070757.6 filed Jun. 23, 2016 Office Action dated Sep. 5, 2019.
EP 11 850 516.3 filed Jul. 19, 2013 Extended European Search Report dated Mar. 4, 2015.
EP 12 803 493.1 filed Jan. 15, 2014 Extended European Search Report dated Mar. 5, 2015.
EP 14875859.2 filed Jun. 9, 2016 Extended European Search Report dated Jul. 31, 2017.
JP 2013-546435 filed Jun. 6, 2013 Office Action dated Aug. 29, 2016.
JP 2014-517229 filed Dec. 20, 2013 First Office Action dated May 24, 2016.
JP 2014-517229 filed Dec. 20, 2013 Notice of Allowance dated Oct. 3, 2016.
KR 10-2014-7001756 filed Jan. 22, 2014 Office Action dated May 18, 2018.
PCT/US2009/068828 filed Dec. 18, 2009 International Preliminary Report on Patentability dated Jun. 21, 2011.
PCT/US2009/068828 filed Dec. 18, 2009 Search Report dated Mar. 3, 2010.
PCT/US2009/068828 filed Dec. 18, 2009 Written Opinion dated Mar. 3, 2010.
PCT/US2011/066940 filed Dec. 22, 2011 International Preliminary Report on Patentability dated Jul. 4, 2013.
PCT/US2011/066940 filed Dec. 22, 2011 International Search Report and Written Opinion dated Apr. 20, 2012.
PCT/US2012/043877 filed Jun. 22, 2012 International Search Report and Written Opinion dated Sep. 24, 2012.
PCT/US2014/072168 filed Dec. 23, 2014 International Search Report and Written Opinion dated Apr. 16, 2015.
U.S. Appl. No. 12/642,456, filed Dec. 18, 2009 Final Office Action dated Nov. 23, 2012.
U.S. Appl. No. 12/642,456, filed Dec. 18, 2009 Non-Final Office Action dated Jul. 2, 2012.
U.S. Appl. No. 12/642,456, filed Dec. 18, 2009 Notice of Allowance dated Jul. 12, 2013.
U.S. Appl. No. 13/335,587, filed Dec. 22, 2011 Decision on Appeal dated Oct. 25, 2017.
U.S. Appl. No. 13/335,587, filed Dec. 22, 2011 Examiner's Answer dated May 16, 2016.
U.S. Appl. No. 13/335,587, filed Dec. 22, 2011 Final Office Action dated Jul. 28, 2014.
U.S. Appl. No. 13/335,587, filed Dec. 22, 2011 Final Office Action dated Jul. 8, 2015.
U.S. Appl. No. 13/335,587, filed Dec. 22, 2011 Non-Final Office Action dated Feb. 2, 2015.
U.S. Appl. No. 13/335,587, filed Dec. 22, 2011 Non-Final Office Action dated Mar. 12, 2014.
U.S. Appl. No. 13/335,587, filed Dec. 22, 2011 Notice of Allowance dated Jan. 17, 2018.
U.S. Appl. No. 13/531,406, filed Jun. 22, 2012 Advisory Action dated May 3, 2017.
U.S. Appl. No. 13/531,406, filed Jun. 22, 2012 Final Office Action dated Feb. 25, 2016.
U.S. Appl. No. 13/531,406, filed Jun. 22, 2012 Final Office Action dated Feb. 27, 2017.
U.S. Appl. No. 13/531,406, filed Jun. 22, 2012 Non-Final Office Action dated Aug. 10, 2016.

(56) References Cited

OTHER PUBLICATIONS

U.S. Appl. No. 13/531,406, filed Jun. 22, 2012 Non-Final Office Action dated Aug. 18, 2015.
U.S. Appl. No. 13/531,406, filed Jun. 22, 2012 Non-Final Office Action dated Jan. 9, 2015.
U.S. Appl. No. 13/531,406, filed Jun. 22, 2012 Notice of Allowance dated Jun. 20, 2017.
U.S. Appl. No. 13/886,196, filed May 2, 2013 Advisory Action dated Jun. 13, 2014.
U.S. Appl. No. 13/886,196, filed May 2, 2013 Decision on Appeal dated Nov. 20, 2017.
U.S. Appl. No. 13/886,196, filed May 2, 2013 Examiner's Answer dated Nov. 3, 2015.
U.S. Appl. No. 13/886,196, filed May 2, 2013 Final Office Action dated Apr. 10, 2014.
U.S. Appl. No. 13/886,196, filed May 2, 2013 Final Office Action dated Dec. 22, 2014.
U.S. Appl. No. 13/886,196, filed May 2, 2013 Non-Final Office Action dated Dec. 19, 2013.
U.S. Appl. No. 13/886,196, filed May 2, 2013 Non-Final Office Action dated Jul. 25, 2014.
U.S. Appl. No. 14/581,019, filed Dec. 23, 2014 Advisory Action dated Jun. 12, 2019.
U.S. Appl. No. 14/581,019, filed Dec. 23, 2014 Advisory Action dated Oct. 17, 2018.
U.S. Appl. No. 14/581,019, filed Dec. 23, 2014 Final Office Action dated Apr. 18, 2019.

50
52
54
18 GA.
2.5 cm
60B
60

50
52
54
60
60A
60B
56

52
54
55
50
18 GA.
2.5 cm 50
55
54
55
70
56
58

50
18
36A
36B
18A

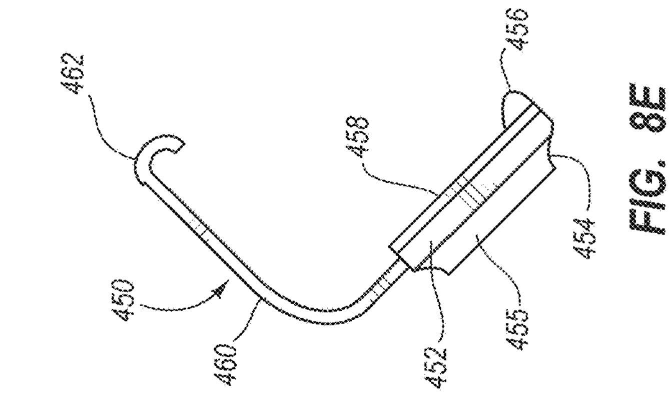
462
456
458
450
454
460
452
455
FIG. 8E
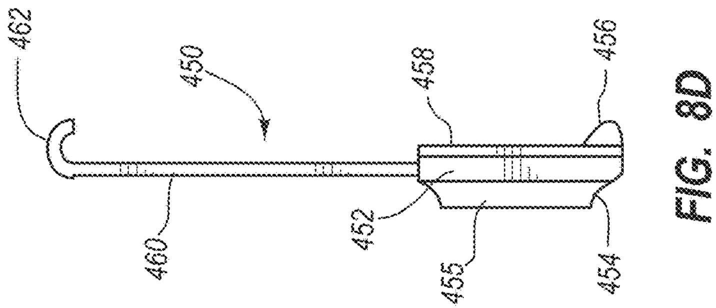
462
450
458
456
452
460
455
454
FIG. 8D
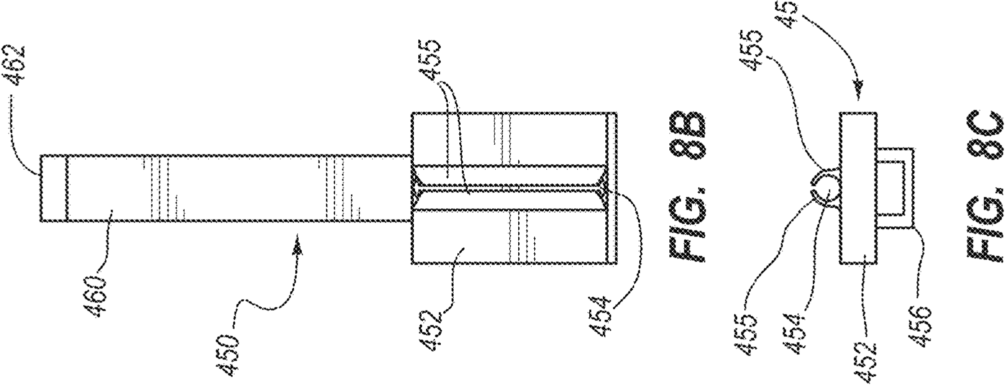
462
455
460
450
452
454
FIG. 8B
455
450
455
454
452
456
FIG. 8C
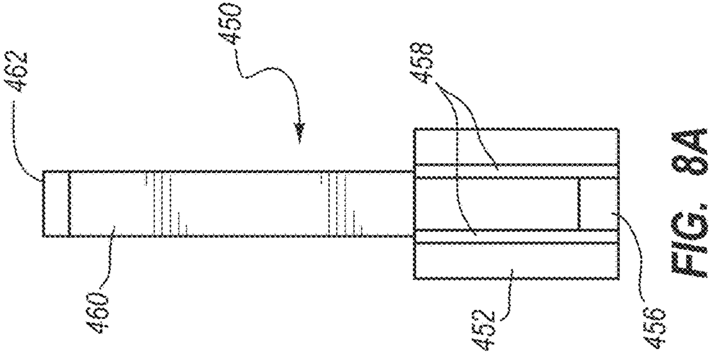
462
450
458
460
452
456
FIG. 8A

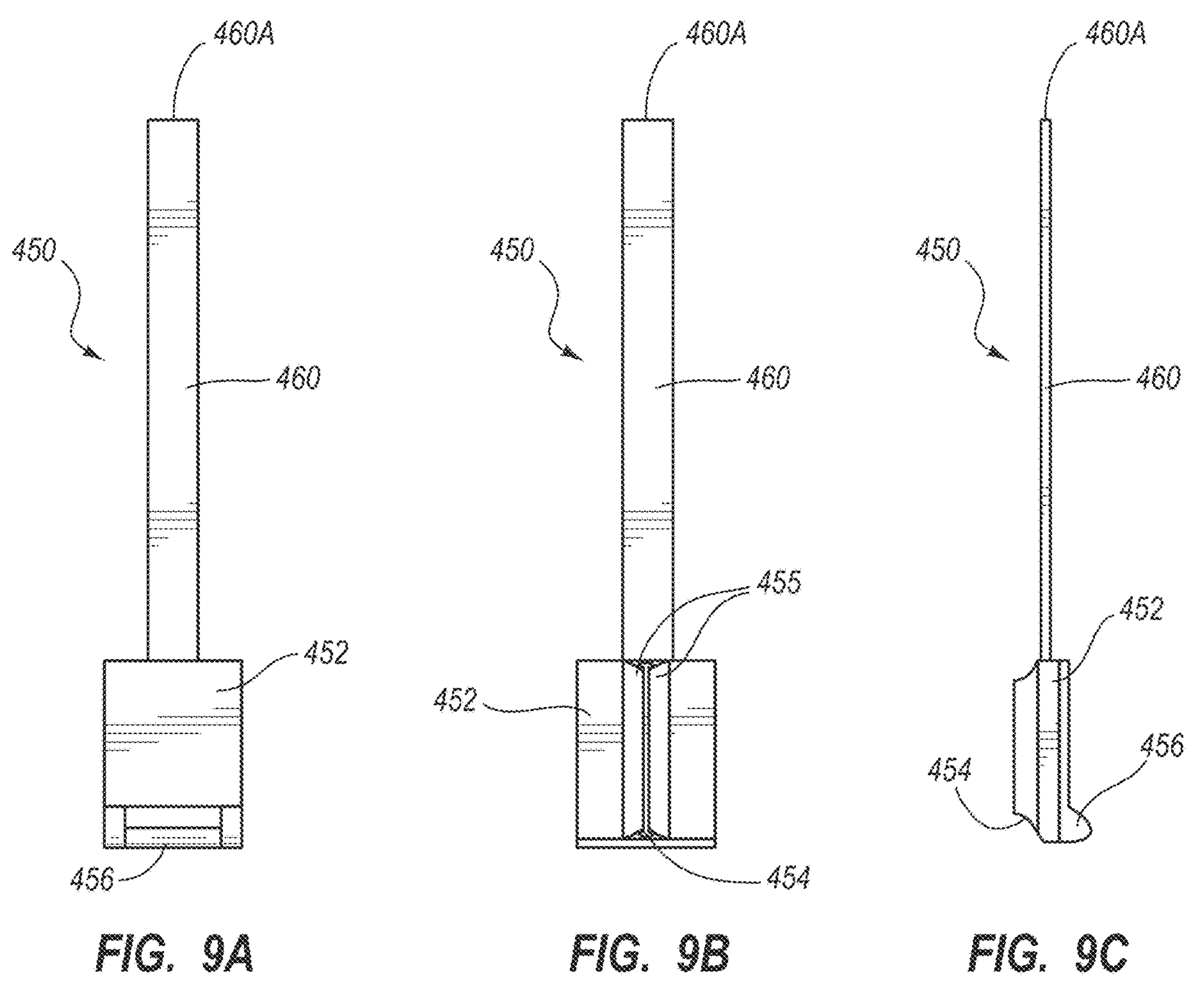
FIG. 9A
FIG. 9B
FIG. 9C
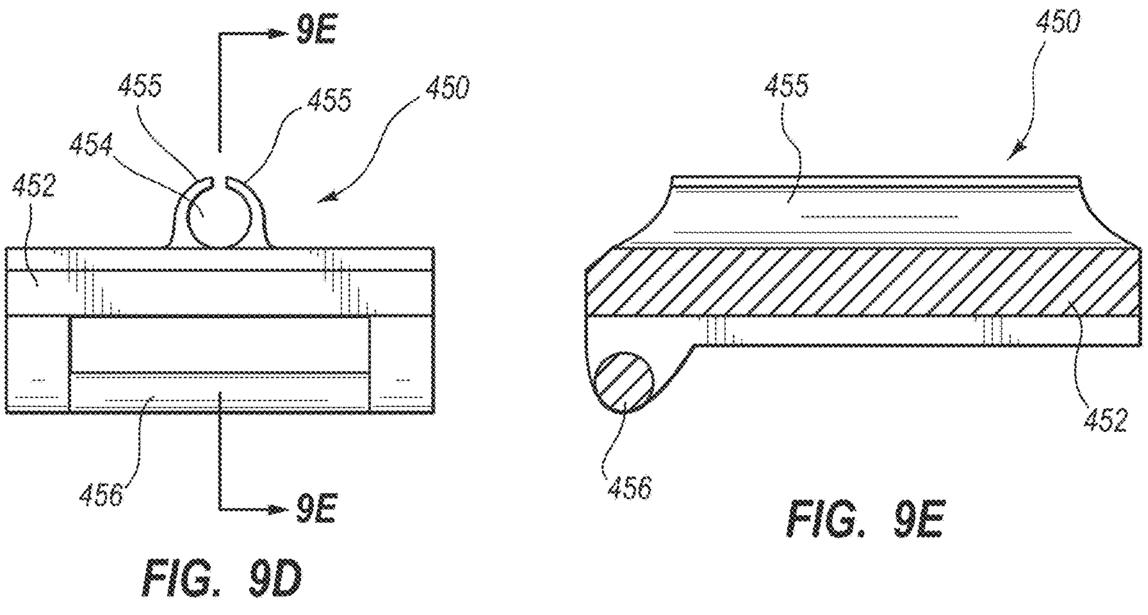
FIG. 9D
FIG. 9E

NEEDLE GUIDES FOR A SONOGRAPHIC IMAGING DEVICE

CROSS-REFERENCE TO RELATED APPLICATIONS

This application is a division of U.S. patent application Ser. No. 16/356,800, filed Mar. 18, 2019, which is a continuation of U.S. patent application Ser. No. 13/886,196, filed May 2, 2013, now U.S. Pat. No. 10,231,697, which is a division of U.S. patent application Ser. No. 12/642,456, filed Dec. 18, 2009, now U.S. Pat. No. 8,574,160, which claims the benefit of U.S. Provisional Application No. 61/138,606, filed Dec. 18, 2008, each of which is incorporated herein by reference in its entirety.

BRIEF SUMMARY

Briefly summarized, embodiments of the present invention are directed to needle guide systems for a sonography device. The needle guide systems include both fixed and adjustable needle guides for use with a probe of the sonography device.

In one embodiment, the needle guide includes a needle guide body that is rotatably mounted to a sonography device probe. A plurality of needle channels is disposed on a surface of the needle guide body. Each needle channel can be selectively rotated into position to guide a needle into a body of a patient at a predetermined needle insertion angle. If another needle insertion angle is desired, the needle guide is rotated to place a new needle channel defining the desired needle insertion angle into position. The needle guide can be permanently or removably attached to the probe.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 5A-6E are various views of an adjustable needle guide system according to one embodiment;

FIGS. 7A-8F are various views of an adjustable needle guide system according to another embodiment;

FIGS. 9A-10F are various views of an adjustable needle guide system according to yet another embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle or catheter placed within the body of a patient is considered a distal end of the needle or catheter, while the needle or catheter end remaining outside the body is a proximal end of the needle or catheter. Also, the words "including," "has," and "having," as used herein, including the claims, shall have the same meaning as the word "comprising."

FIGS. 1-11D depict various features of embodiments of the present invention, which are generally directed to needle guide systems for use with a sonographic imaging device in assisting the percutaneous insertion of a needle or other medical device into a body portion, such as a vasculature of a patient, for instance.

Figure 1:
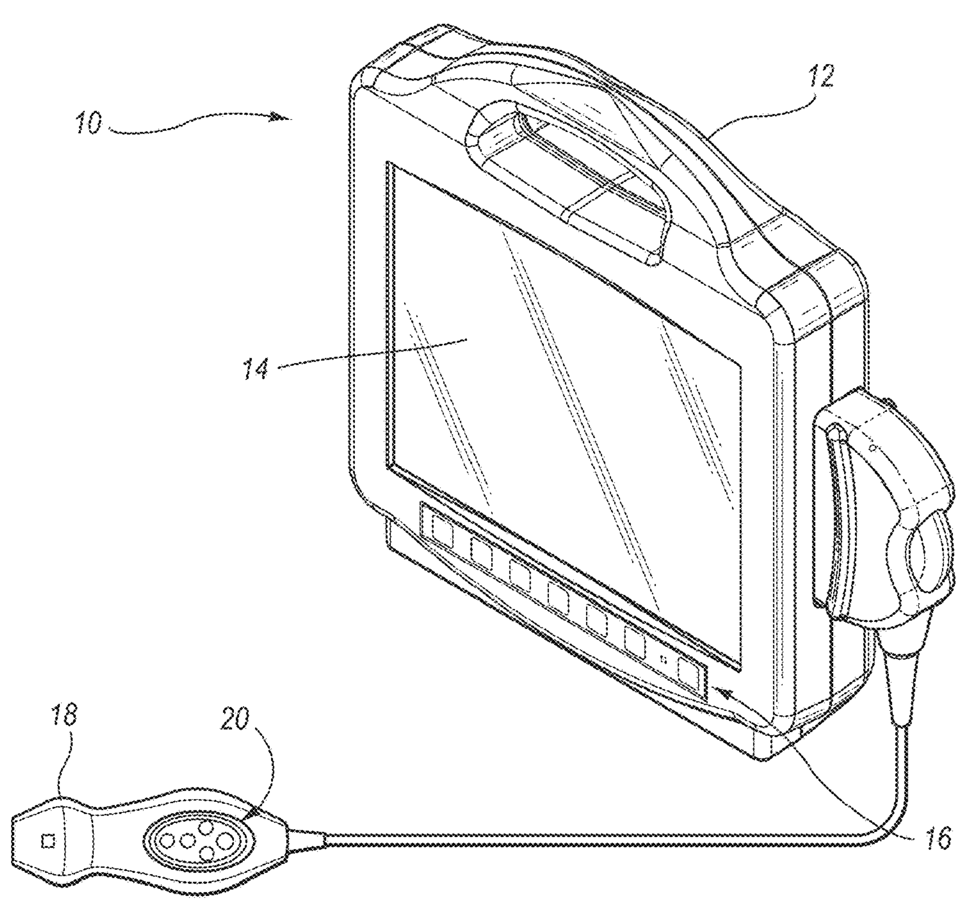
FIG. 1 is simplified perspective view of a sonographic imaging system that serves as an example environment in which embodiments of the present invention can be practiced.

Reference is first made to FIG. 1 in describing a sonographic imaging system ("system"), generally described at 10, for ultrasonically imaging portions of a patient body. The system 10 includes a console 12 including a display 14 and one or more user input controls 16. In one embodiment, the system 10 also includes a probe 18 including one or more user controls in the form of control buttons 20. Briefly, the probe 18 is configured to transmit ultrasonic signals from a head portion 18A thereof into a portion of a patient body and to receive the ultrasonic signals after reflection by internal structures of the patient body. The system 10 processes the reflected ultrasonic signals for depiction on the display 14.

The user input controls 16 of the console 12 may include, for example, image gain controls to adjust the amplification of a received ultrasonic signal, image depth controls to image structures at different depths and adjust the focus of an ultrasonic image displayed on the display 14, depth marker controls to selectively display depth markers and/or grid lines, print and/or save controls to print/save an image currently displayed on the display, image freeze controls to pause an image currently displayed on the display, time/date set controls, and other controls for operating the system 10. Corresponding controls, or a subset thereof, are also included in the control buttons 20 on the probe 18. In addition, in other embodiments the functionality of the user input controls 16 can be provided by a keyboard, mouse, or other suitable input device.

Figure 2:
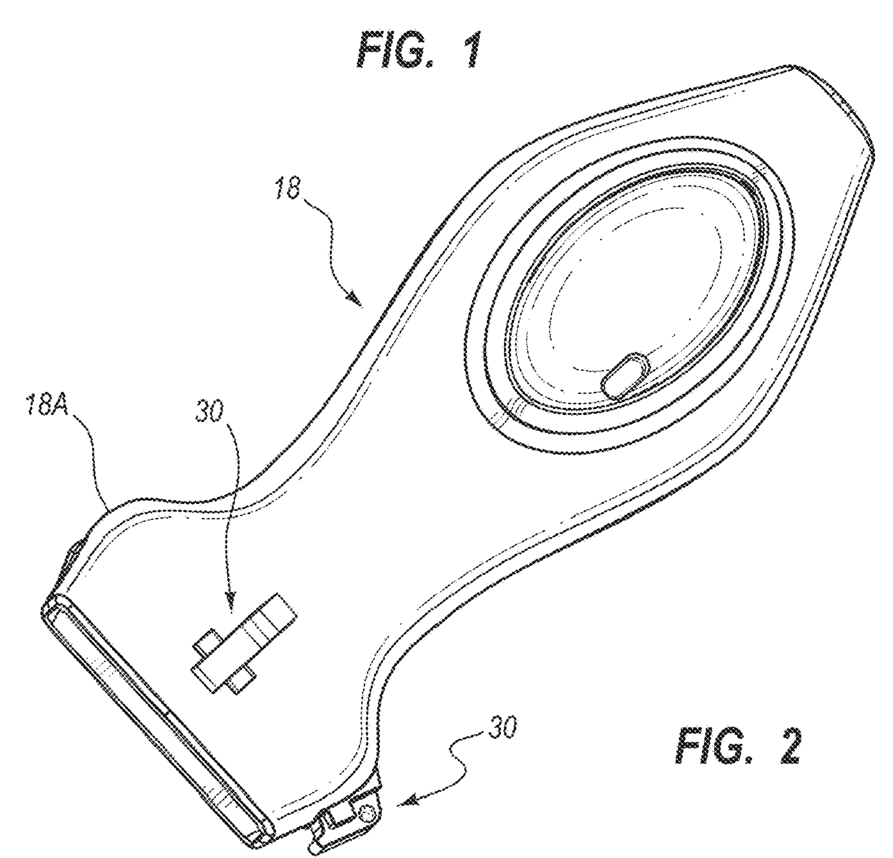
FIG. 2 is a perspective view of a handheld probe of the system of FIG. 1.

FIG. 2 shows the probe 18 of FIG. 1, including two needle guide connectors 30 that are included as part of a needle guide mounting system configured in accordance with one example embodiment. The needle guide connectors 30 are included on front and side portions of the probe 18 but are identically configured in the present embodiment. As such, the details of only one of the connectors will be described in detail here. It should be appreciated that in other embodiments the needle guide connectors may differ in size, configuration, the number included on the probe, etc. In addition, the design and configuration of the probe is merely one example of an ultrasonic probe that can benefit from the principles described herein.

Figure 3A:
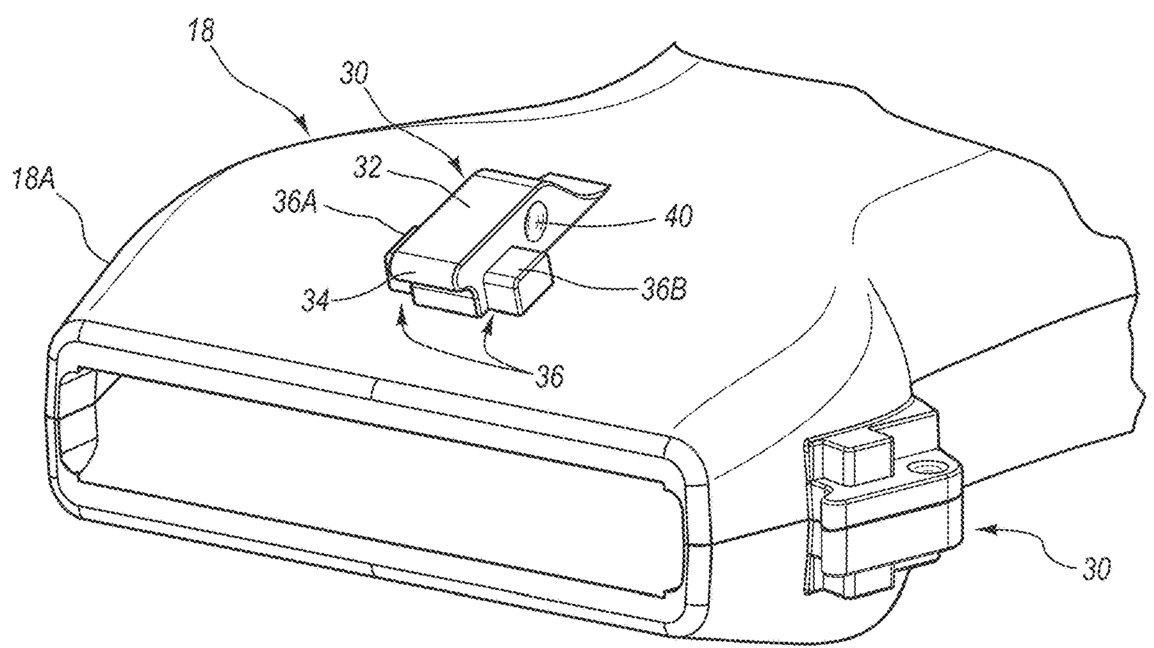
FIGS. 3A and 3B are various views of a portion of a needle guide system included on a handheld probe according to one example embodiment, included on the probe of FIG. 2.
Figure 3B:
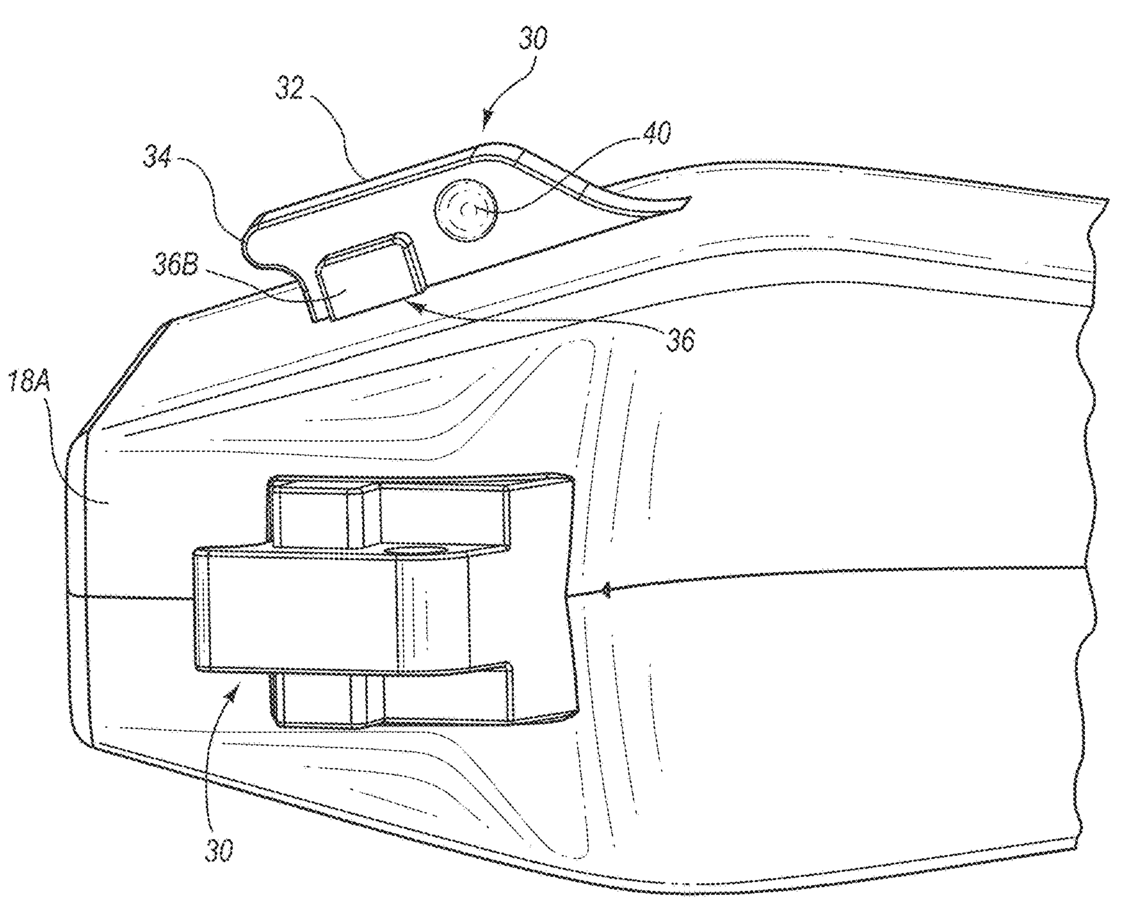

FIGS. 3A and 3B give further details of the needle guide connectors 30 according to one embodiment. Each connector 30 includes an elongate first mounting surface 32, extending from the surface of the probe head portion 18A, which is configured to receive a needle guide thereon, as will be described. An overhang 34 is defined at an end of the mounting surface 32 for assistance in maintaining engagement of the needle guide with the connector 30. A second mounting surface 36 is also included on the each connector 30, which surface defines two stability extensions 36A, 36B. In the present embodiment, the stability extensions 36A, 36B are integrally formed with the first mounting surface 32 and extend along an axis in a direction that is substantially orthogonal to a longitudinal axis of the first mounting surface. So configured, the second mounting surface 36, as defined by the stability extensions 36A and 36B, also extends substantially orthogonal to the first mounting surface 32, though in other embodiments the two mounting surfaces can be aligned at other angles with respect to one another. Note that the size, number, and orientation of the second mounting surface and its respective stability extensions with respect to the first mounting surface can vary from what is explicitly described herein.

One or more depressions 40 are defined on side surfaces of the first mounting surface 32 for engagement with corresponding protrusions defined on the needle guide, as will be described. Of course, other configurations for maintaining engagement between the needle guide and the mounting surfaces of the needle guide connector 30 can also be employed.

Reference is now made to FIGS. 4A-4D, which depict various details of a needle guide, generally designated at 50, in accordance with one example embodiment. As shown, the needle guide 50 includes a top surface 52 on which a needle channel 54, defined by two lips 55, is defined for guiding a needle to a body portion imaged by the system 10 via percutaneous insertion. The top surface 52, and therefore the needle channel 54, is angled with respect to a longitudinal axis of the probe 18 so as to enable the needle to intercept the targeted body portion at a depth as determined by the ultrasonic imaging performed by the system 10. The needle insertion angle defined by the needle channel 54 can vary according to the configuration of the needle guide. Thus, selection of an appropriately angled needle guide is determined by the depth of the intended subcutaneous target within the patient body to be intercepted. As such, the specific size and configuration details of the needle guide described herein are merely examples.

Figures 4A, 4B, 4C, 4D, 4E:
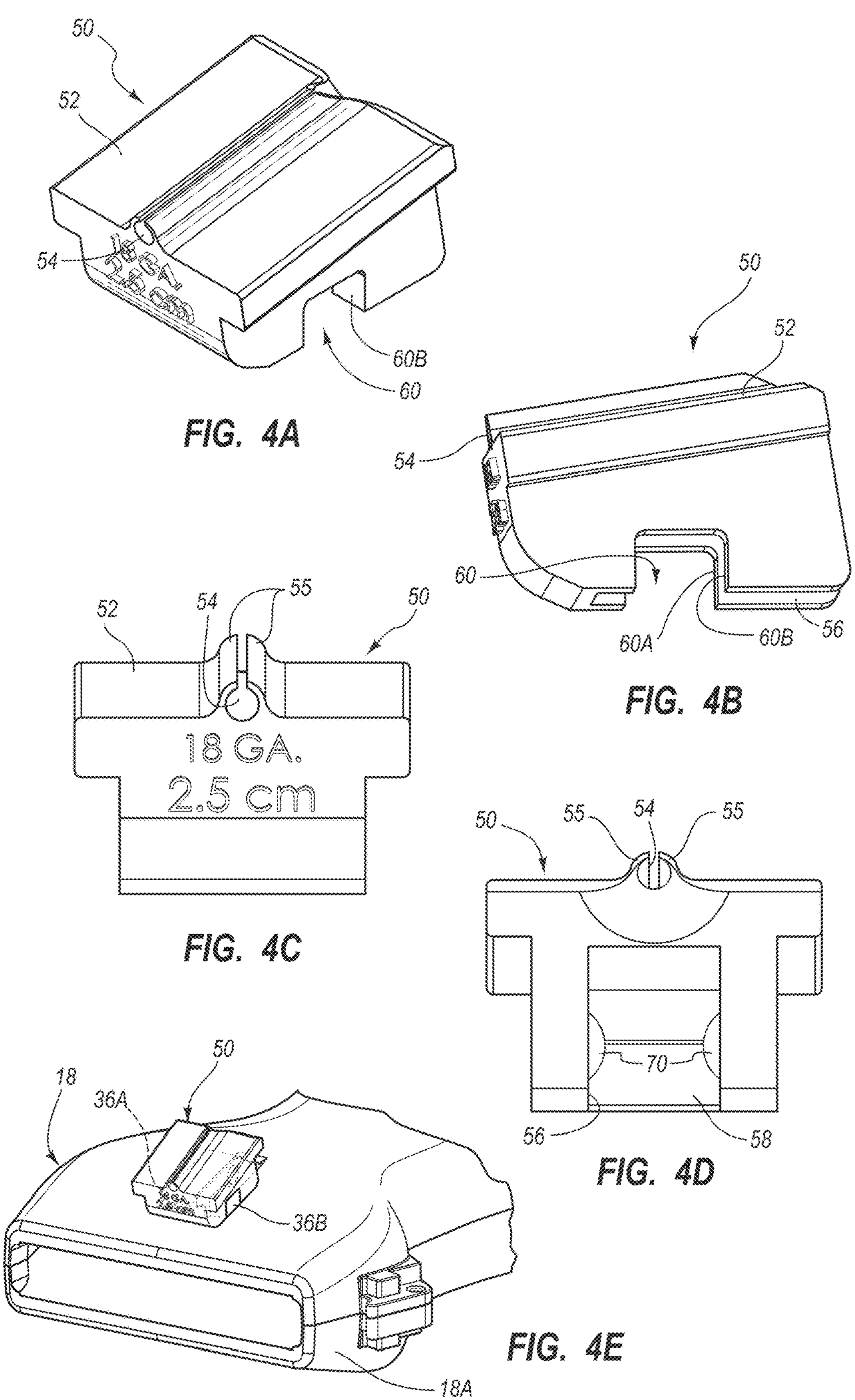
FIGS. 4A-4D are various views of a needle guide for use with the handheld probe shown in FIGS. 3A and 3B, according to one embodiment.
FIG. 4E is a perspective view of the needle guide of FIGS. 4A-4D attached to the probe of FIG. 2.

The needle guide 50 defines a first cavity 56, best seen in FIG. 4D, which is shaped to receive therein the first mounting surface 32 of the connector 30 when the needle guide is removably attached to the probe 18. A smoothly shaped extended surface 58 is included at the closed end of the cavity 56 and is configured for interfacing with the smoothly shaped overhang 34 of the first mounting surface 32 in retaining the needle guide 50 on the connector 30 when attached thereto. The extended surface 58 and overhang 34 can be configured in a variety of ways so as to assist in retaining the needle guide on the connector 30.

A second cavity 60, which crosses substantially orthogonally the first cavity 56 and includes notches 60A, 60B, is defined by the body of the needle guide 50, as best seen in FIG. 4B. The notches 60A, 60B of the second cavity 60 are positioned to respectively receive therein the stability extensions 36A, 36B when the needle guide 50 is attached to the needle guide connector 30, such as in a snap-fit configuration for instance, as shown in FIG. 4E. So attached, the stability extensions 36A, 36B of the connector 30 engage the notches 60A, 60B and this engagement, together with the engagement of the first mounting surface 32 with the needle guide cavity 56, secures the needle guide in place with respect to the probe 18. This in turn provides a stable needle guide structure that resists undesired movement, such as the needle guide undesirably slipping off the probe in a direction parallel to a longitudinal axis of the probe 18. Thus, the needle guide remains in place to enable a clinician to insert a needle or other medical instrument into the target area of the patient body via the needle channel 54 while the target area is imaged by the sonography system 10. It is appreciated that the angle of intersection between the first cavity 56 and the second cavity 60 of the needle guide 50 should be configured to match the angle of intersection between the first mounting surface 32 and the second mounting surface 36 of the needle guide connector 30 of the probe 18 in all cases, regardless of whether the angle of intersection is orthogonal.

The needle guide 50 further includes protrusions 70 in the first cavity 56 that are sized and positioned to engage with the depressions 40 (FIGS. 3A, 3B) of the needle guide connector 30 when the needle guide is attached to the needle guide connector 30. Note that the size, shape, number, and other configuration details of the needle guide cavities can vary from what is described herein while still residing within the scope of present embodiments. For instance, the shape defined by the notches 60A, 60B, can be triangular, rounded, etc., instead of the square configuration shown here.

The needle channel 54 of FIGS. 4A-4E is shown to be sized for an 18 Gauge needle. In other embodiments, however, the needle channel can be sized to accommodate needles of other sizes and configurations. Also, the needle guide can be configured in one embodiment to accept devices other than needles, such as trocars or catheters for instance. As mentioned above, the needle guide top surface can be configured such that the needle channel defines an angle with a longitudinal axis of the probe 18 different from what is shown in FIGS. 4A-4E. As such, multiple needle guides, each having a needle channel defining a unique angle with the longitudinal axis of the probe 18, can be constructed as to be selectively attachable to/removable from the probe needle guide connector 30 of the probe 18, enabling a plurality of needle insertion angles to be achieved with the system 10.

Figures 5A, 5B, 6A, 6B, 6C:
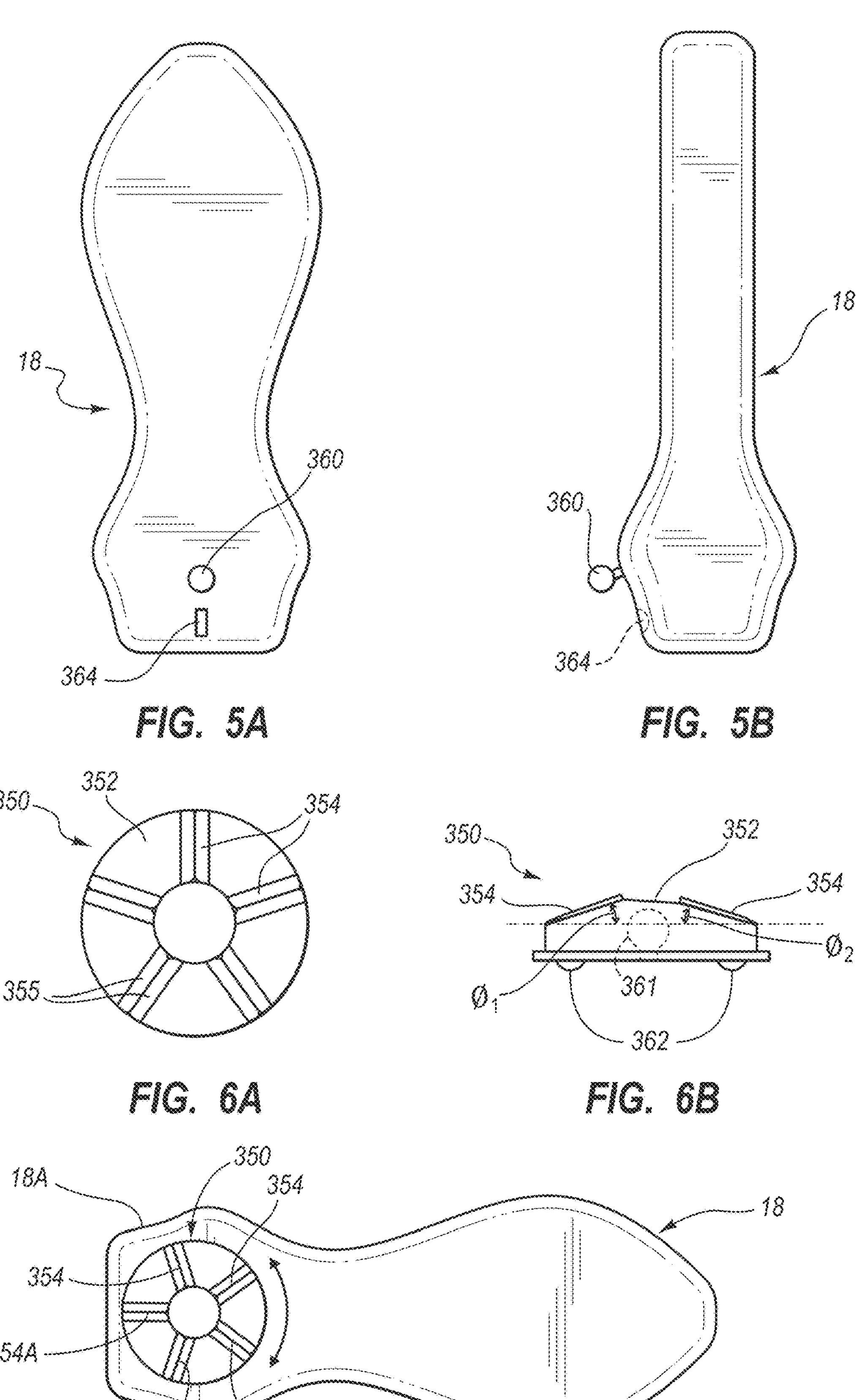

Reference is now made to FIGS. 5A-6E in describing a needle guide system according to another embodiment. FIGS. 5A and 5B show the probe 18 including a mounting component, such as a mounting ball 360 (see also mounting ball 361 in FIGS. 6B, 6D, and 6E), on the probe head portion 18A for rotatably receiving a rotatable needle guide 350, shown in FIGS. 6A and 6B. As shown, the needle guide 350 includes a circular body that defines a chamfered or slanted top surface 352. A plurality of needle channels 354 is included on the top surface. Each needle channel 354 is defined by two lips 355 or other suitable structure. The top surface 352 is configured such that each needle channel 354 is positioned at a unique angle. For instance, FIG. 6B shows one needle channel 354 of the needle guide 350 angled to define a deflection angle $\phi_1$ with respect to horizontal and another needle channel 354 angled to define a deflection angle $\phi_2$ with respect to horizontal, from the perspective shown in FIG. 6B. As will be seen, this enables the needle guide to guide a needle into the patient body at one of a plurality of different needle insertion angles, measured with respect to a longitudinal axis of the probe 18 to which the needle guide is either removably or permanently attached. In the illustrated embodiment, five needle channels 354 are included on the top surface 352 of the needle guide 350, though more or fewer than this can be included. Also, though shown distributed in a star pattern, the distribution of the needle channels on the needle guide top surface can vary from what is shown and described herein.

As mentioned, the needle guide 350 is configured to attach to a fixture on the probe 18, such as the mounting ball 360 shown in FIGS. 5A and 5B (see also mounting ball 361 in FIGS. 6B, 6D, and 6E) or other suitable structure, such that the needle guide 350 is rotatable with respect to the probe. The fixture can be placed on any suitable surface of the probe 18. One or more protrusions 362 are included on a bottom surface of the needle guide 350 and are each positioned so as to engage a depression 364 defined on the surface of the probe head portion 18A and thus secure the needle guide in a particular position until moved by a force sufficient to overcome the friction engagement between the corresponding protrusion and the depression. So configured, a clinician may rotate the needle guide 350, as shown in FIG. 6C, until the desired needle channel 354 having the desired insertion angle is aligned at a usable position 354A to enable the clinician to insert a correspondingly sized needle into the patient body via the selected needle channel to intercept an imaged target area of the patient body at a predetermined depth. Note that the location, number, and configuration of the protrusions and depressions can vary from what is shown and described.

Figures 6D, 6E:
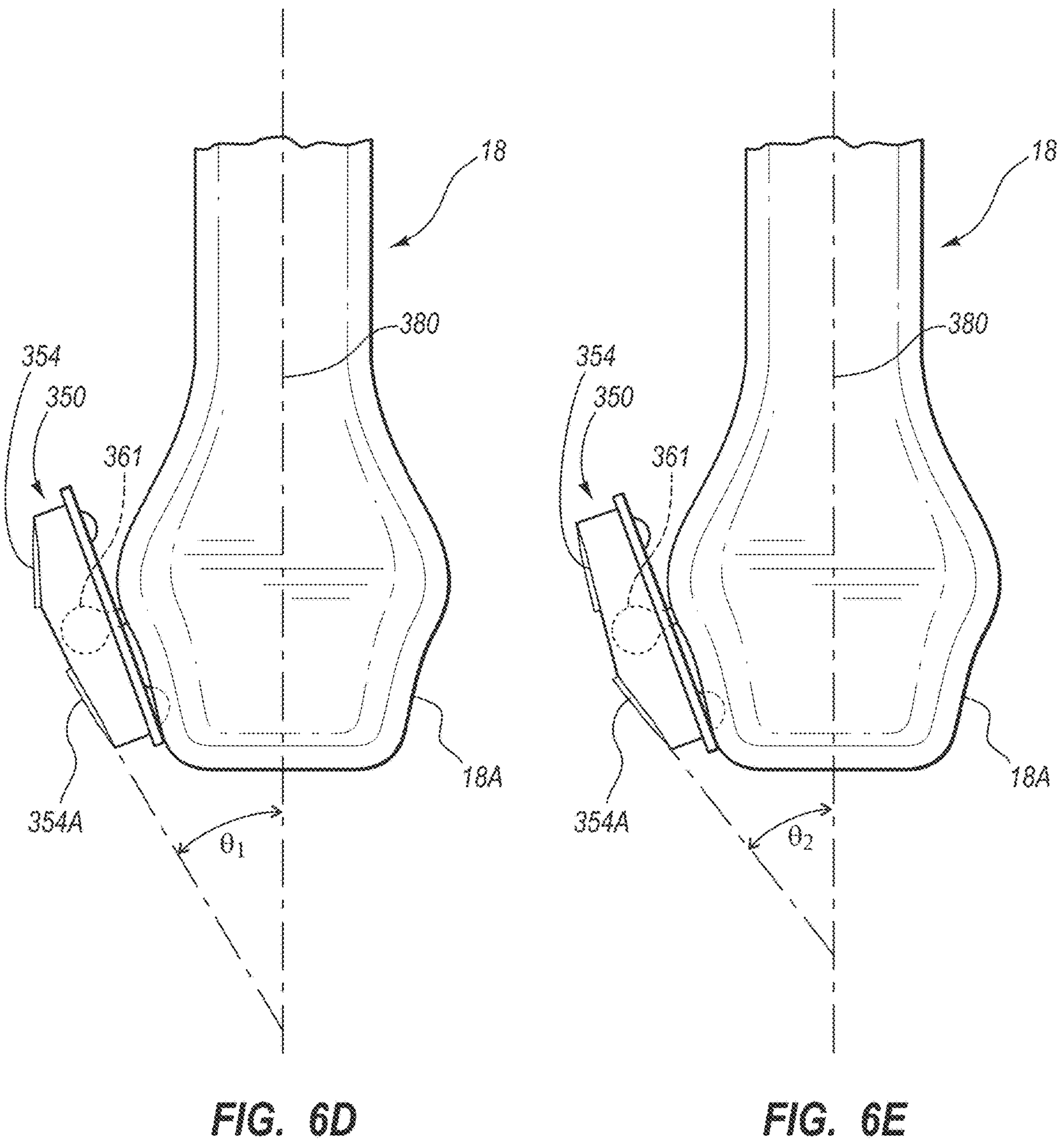

FIGS. 6D and 6E show how the needle guide 350 enables needle insertions of different angles of entry into the patient body. In FIG. 6D, one of the needle channels 354 is positioned for use, i.e., in the position 354A (see FIG. 6C) such that it defines a needle insertion angle $\theta_1$ with the longitudinal axis 380 of the probe 18. In contrast, FIG. 6E shows another needle guide channel 354 in the position 354A, which defines a needle insertion angle $\theta_2$ with the probe longitudinal axis 380. As can be seen from FIGS. 6D and 6E, the needle path enabled by the needle channel 354 of FIG. 6D penetrates more deeply relative to the needle path enabled by the needle channel 354 of FIG. 6E. As such, the needle channel 354 of FIG. 6D can be employed in order to enable a needle to intercept a target area of the patient body that is relatively deeper, while the needle channel shown in FIG. 6E can be employed to intercept a relatively shallower target area.

Thus, in accordance with the present embodiment, the needle guide 350 can be used to direct a needle to a proper depth within the patient body during use of the probe 18 and system 10. In particular, once a target area of the patient body has been located by the probe 18 and imaged by the system 10, the clinician rotates the needle guide 350 until a desired one of the needle channels 354 having a desired needle insertion angle with respect to the longitudinal axis 380 of the probe 18 is in the position 354A and ready for use. The clinician can then insert the needle into the needle channel 354, which channel guides the needle into the patient body at the desired needle insertion angle until the needle intercepts the target area.

Note that the shape and size of the needle guide can vary from what is described here. For instance, the general shape of the needle guide can be hexagonal, pentagonal, triangular, square, or other geometric shape in one embodiment. Also, the needle guide can be reduced in size from what is shown in FIGS. 6D and 6E in order to match a configuration of the sonographic probe. The needle channels can each be sized to accommodate needles of differing gauges in one embodiment.

Reference is now made to FIGS. 7A-8E in describing a needle guide system according to another embodiment. In particular, FIGS. 8A-8E show a needle guide 450, which generally includes a base 452 and a flexible extension 460. The base 452 includes on a top surface thereof a needle channel 454 defined by lips 455 and on a bottom surface a connector 456 for attaching the needle guide 450 to the probe 18 and longitudinally extending stability rails 458 for preventing twisting or torsion of the needle guide during use on the probe. The flexible extension 460 is an elongate member that longitudinally extends from the base 452 and includes a first engagement feature, such as a hook 462, at a free end 460A of the extension.

Figures 7A, 7B:
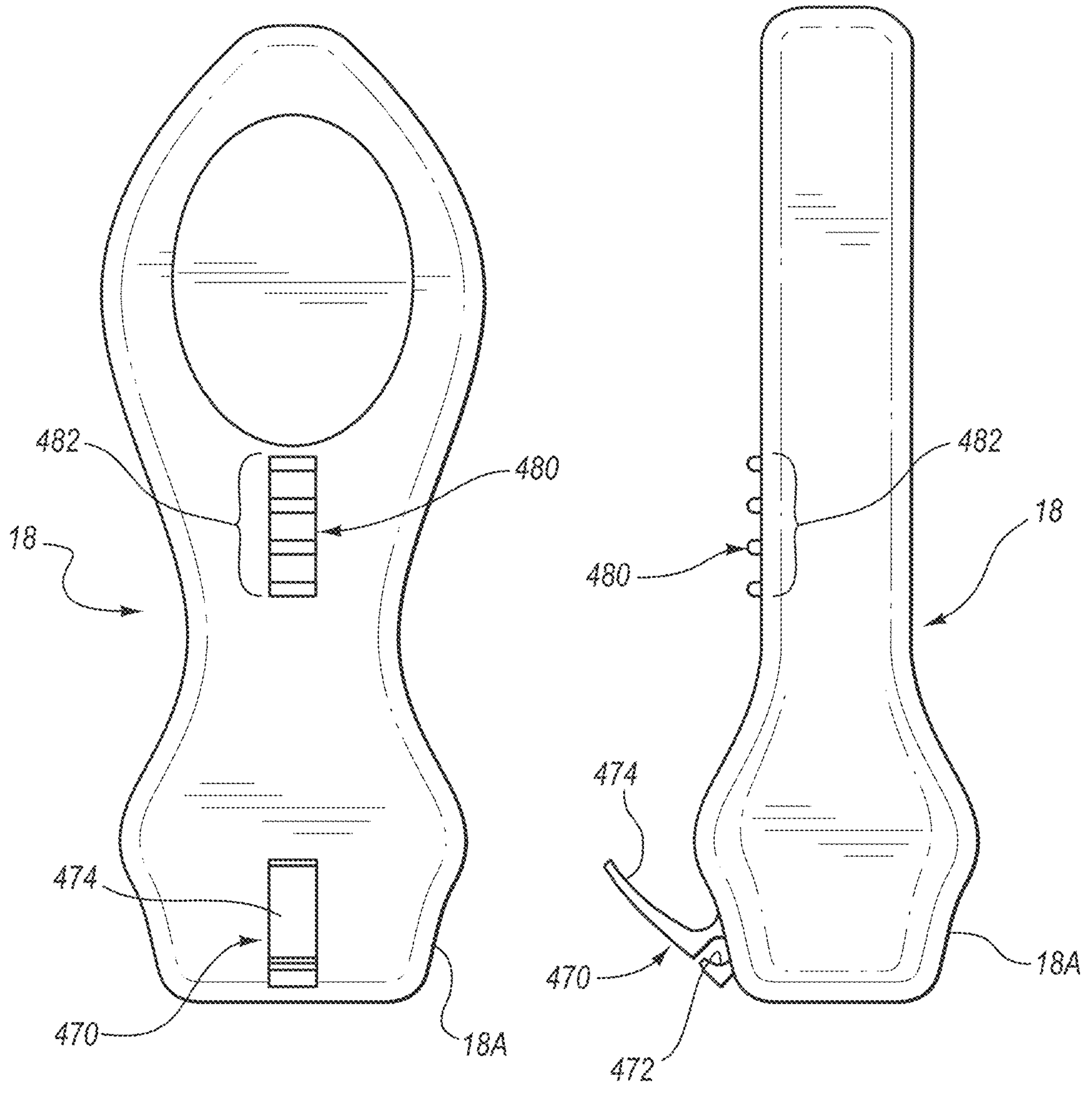
Figure 8F:
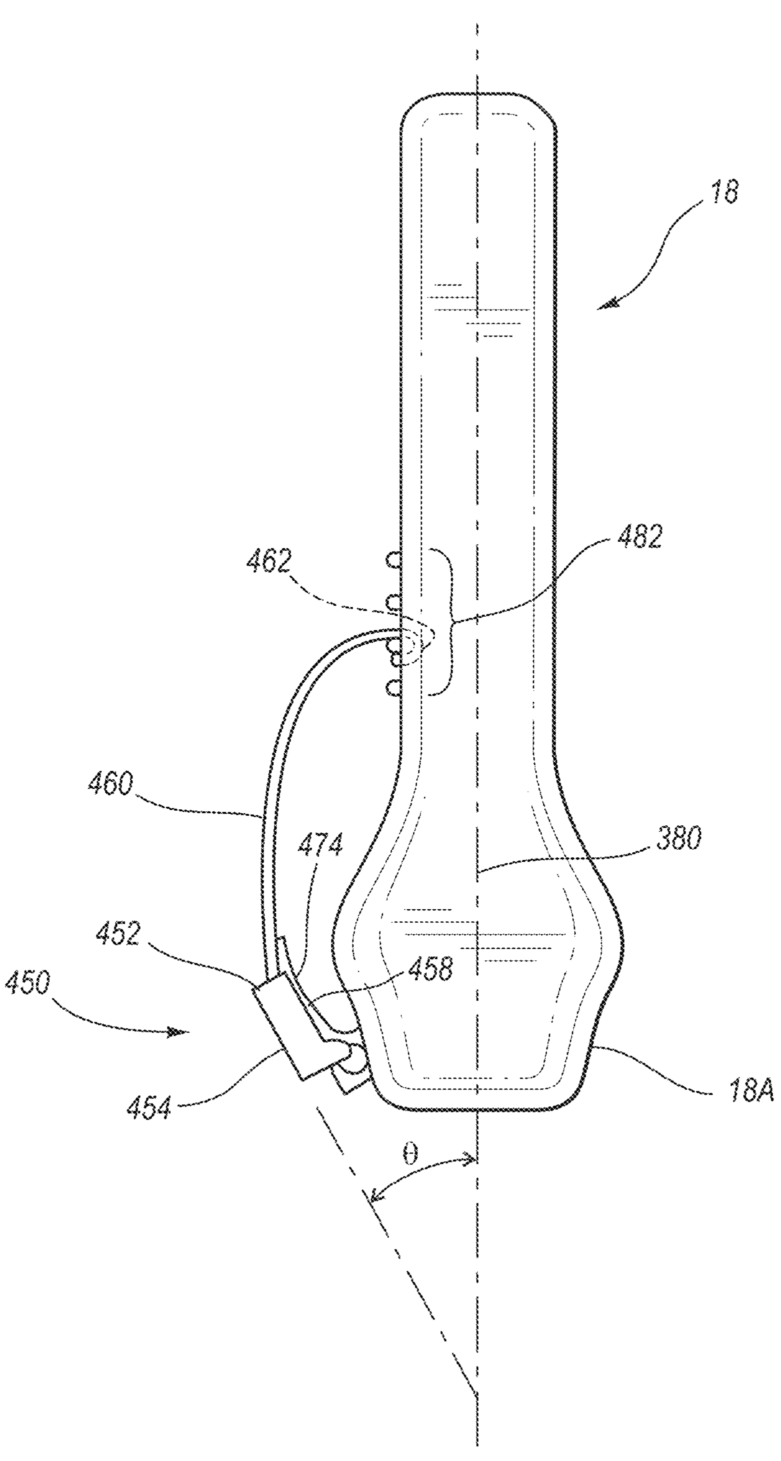

As shown in FIGS. 7A and 7B, in the present embodiment the probe 18 includes on its head portion 18A a connector 470 to which the needle guide can removably attach. The connector 470, which itself can be removably or permanently attached to the probe 18, includes a cavity 472 for receiving the connector 456 of the needle guide base 452, and a support arm 474 proximally extending at an acute angle from the probe surface. The probe 18 further includes a receiver array 480, which includes a second engagement feature, configured here as a plurality of spaced apart bars 482 with which the needle guide hook 462 can engage, as shown in FIG. 8F, for example. Specifically, FIG. 8F shows the needle guide 450 attached to the probe 18 via engagement of its connector 456 with the cavity 472 of the probe connector 470. The hook 462 of the needle guide flexible extension 460 is shown engaged with one of the hook receiving bars 482 of the receiver array 480, thus creating an attachment between the first engagement feature of the needle guide, i.e., the hook 462, and the second engagement feature of the probe, i.e., one of the bars 482.

So configured, the needle channel 454 of the needle guide is oriented to define a needle insertion angle $\theta$ with the probe longitudinal axis 380. Note that the extension 460 is configured to be flexible enough to allow for the bending thereof as shown in FIG. 8F. The support arm 474 in the current embodiment is resilient while also providing the needed rigidity for the needle guide base 452 so as to maintain the needle channel 454 in a substantially fixed location after the angle of the needle guide 450 has been selected and set. Additionally, the stability rails 458 straddle the support arm 474 to prevent undesired twisting or torsion of the needle guide 450 during use.

Should it be desired to change the needle insertion angle defined by the needle channel 454, the hook 462 can be manually moved to engage another of the bars 482 of the probe receiver array 480. This in turn alters the needle insertion angle and the depth to which the needle will be inserted into the patient body by the clinician. Generally, in the present embodiment movement of the hook 462 to more proximal bars 482 lessens the needle insertion angle, which in turn enables the needle to penetrate to a relatively deeper target area in the patient body. Of course, the needle guide system can be configured such that a different relationship exists between movement of the needle guide components and the needle insertion angle. Indeed, in one embodiment the adjustable engagement feature can be included on the needle guide itself instead of on the probe, as is the case with the embodiment described here.

FIGS. 9A-9E depict a variation of the needle guide 450, wherein the free end 460A of the flexible extension 460 serves as a first engagement feature of the needle guide in contrast to the hook of the previous embodiment, and wherein a receiver array 580 on the probe 18 includes a second engagement feature implemented as a plurality of slots 582 instead of the bars of the previous embodiment. Further, the needle guide 450 shown in FIGS. 9A-9E is designed for use with a probe connector that includes no support arm, such as the support arm 474 shown in FIGS. 7A-8F. Instead, the flexible extension 460 in the present embodiment is configured so as to be more rigid, relative to the flexible extension of the embodiment depicted in FIGS. 7A-8F, thus enabling it to bend to engage the receiver array 580 while maintaining the needle guide base 452 at a desired position.

Figure 10A:
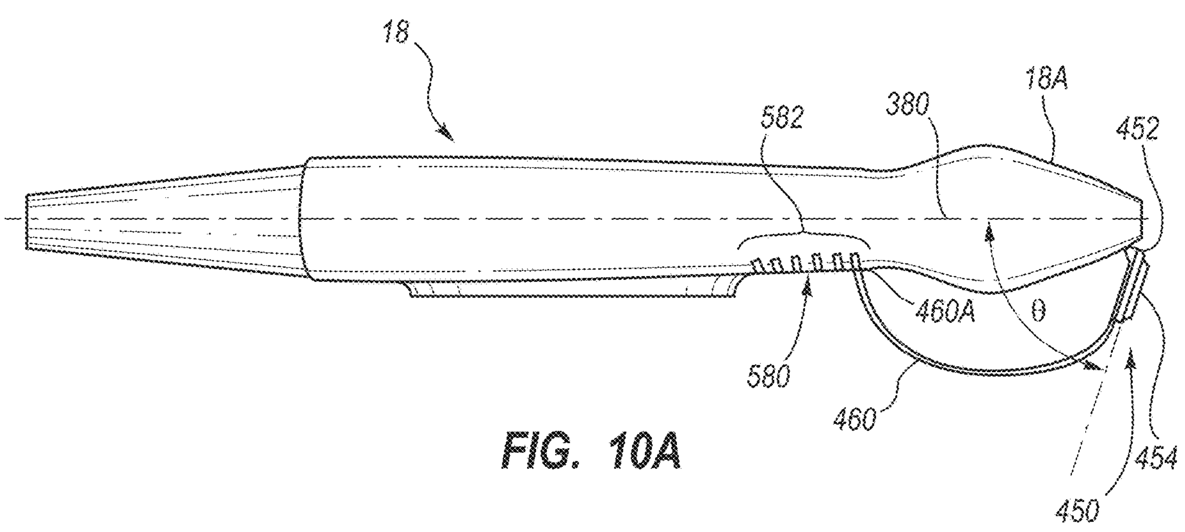
Figure 10B:
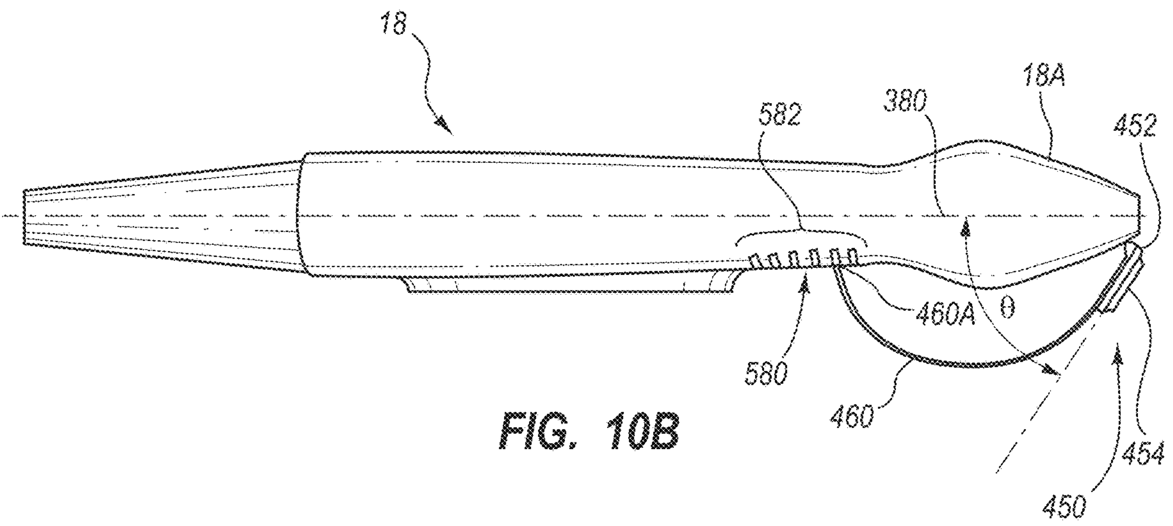
Figure 10C:
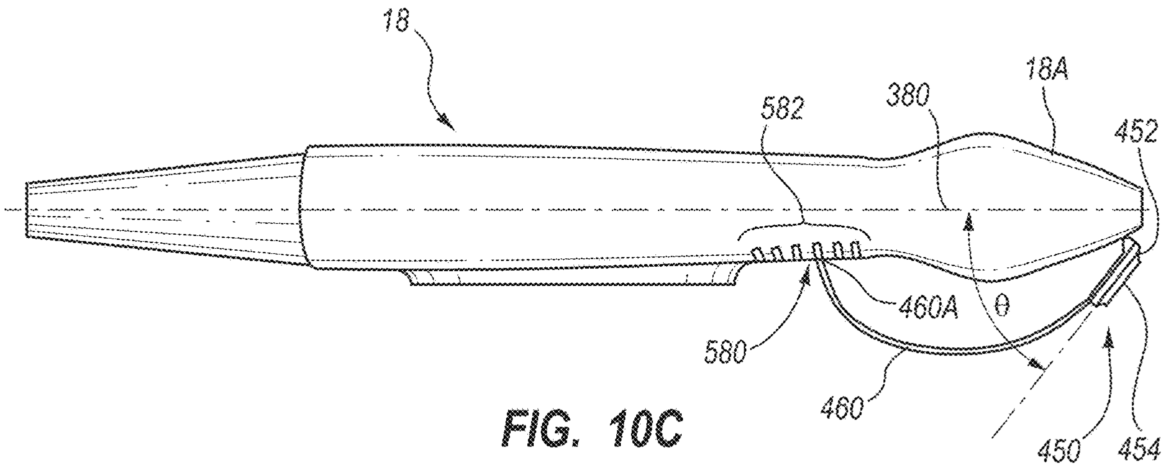
Figure 10D:
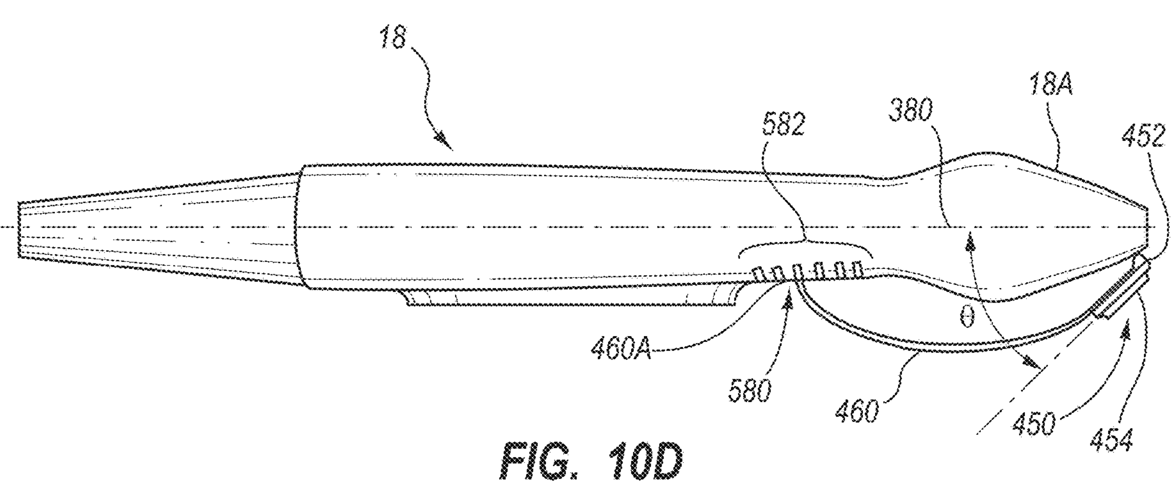
Figure 10E:
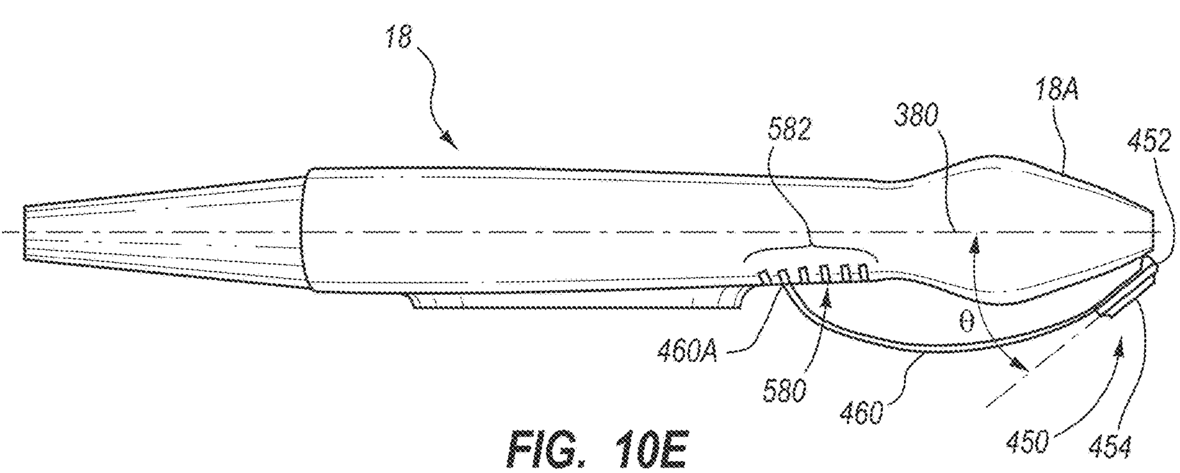
Figure 10F:
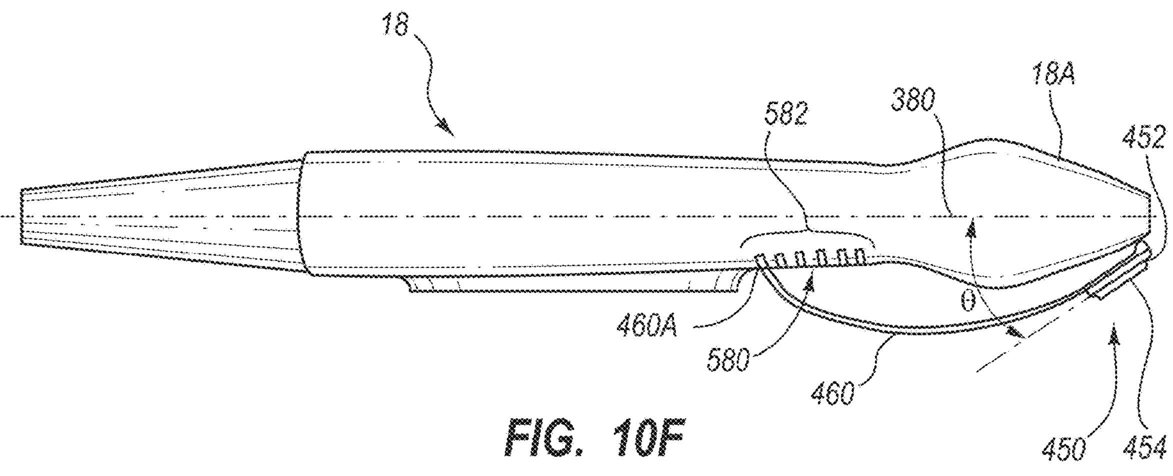

In greater detail, FIGS. 10A-10F show the manner of engagement of the needle guide 450 with the probe 18, according to the first and second engagement features just described above in connection with FIGS. 9A-9E. Note that in FIGS. 10A-10F, the probe connector for attachment of the needle guide has been removed for clarity. In particular, FIG. 10A shows the flexible extension 460 positioned such that the free end 460A thereof is received into the distal-most slot 582 of the probe receiver array 580. This causes the needle guide base 452 and the needle channel 454 disposed thereon to be positioned such that the needle channel defines a relatively large needle insertion angle θ with respect to the probe longitudinal axis 380, which corresponds to inserting a needle in a relatively superficial target area of the patient body located proximate the skin surface thereof.

FIGS. 10B-10F show that as the flexible extension free end 460A of the needle guide 450 is inserted into progressively more proximal slots 582 of the probe receiver array 580, the needle insertion angle θ is reduced, which corresponds to directing the needle to progressively deeper target areas of the patient body. As such, the slots 582 and needle guide 450 can be configured so as to position the needle channel 454 to define predetermined needle insertion angles. In one embodiment, for example, the needle guide system as described in connection with FIGS. 9A-10F can define needle insertion angles ranging from about three degrees to about 43 degrees, though it is appreciated that a variety of possible angles can be achieved. It is noted that the first and second engagement features of the needle guide and probe that are used to interconnect the two can vary from what is described herein, as appreciated by one skilled in the art.

Figure 11A:
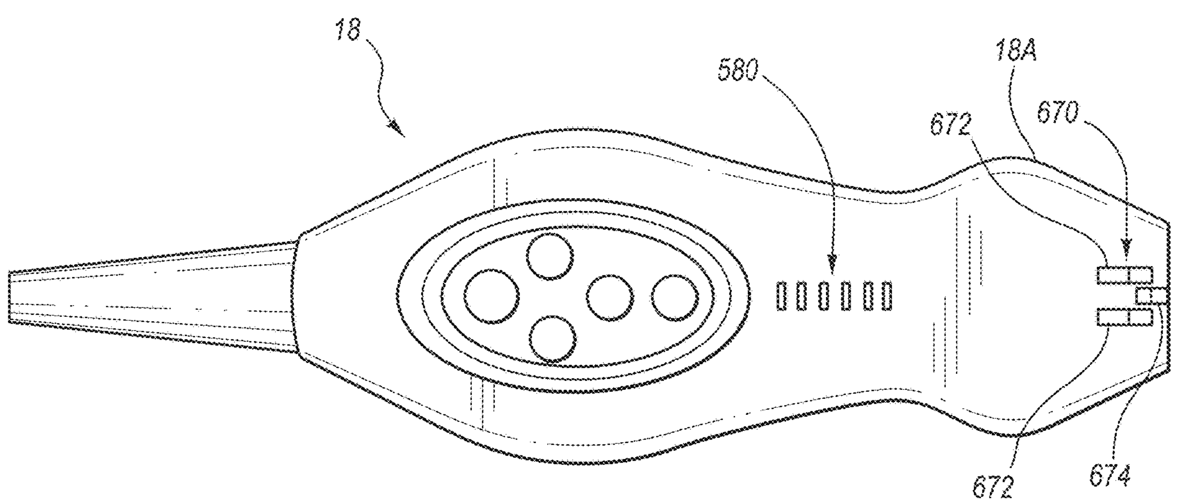
FIGS. 11A-11D show additional details of a needle guide system according to one embodiment.
Figure 11B:
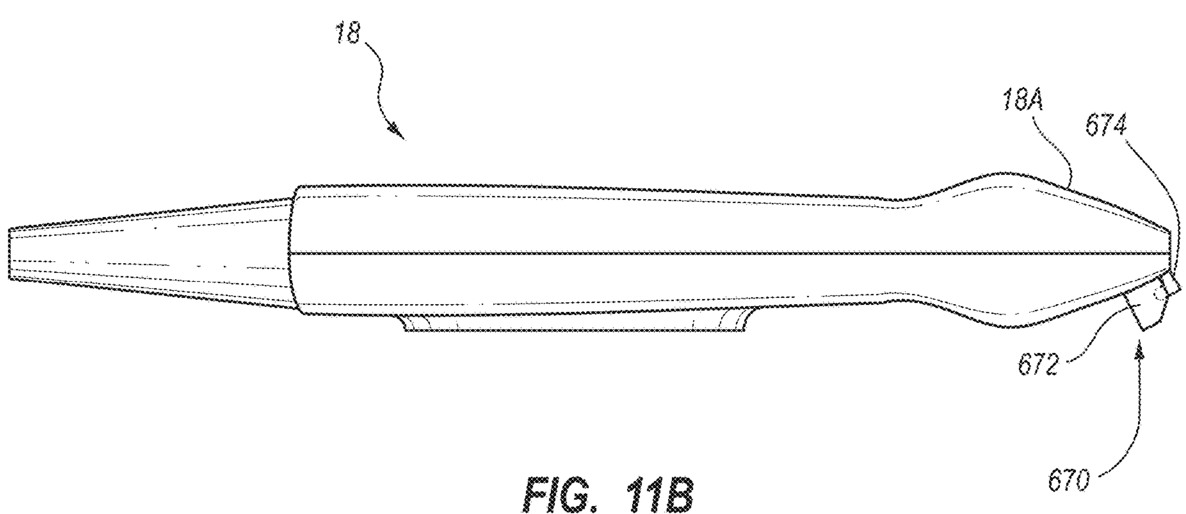
Figure 11C:
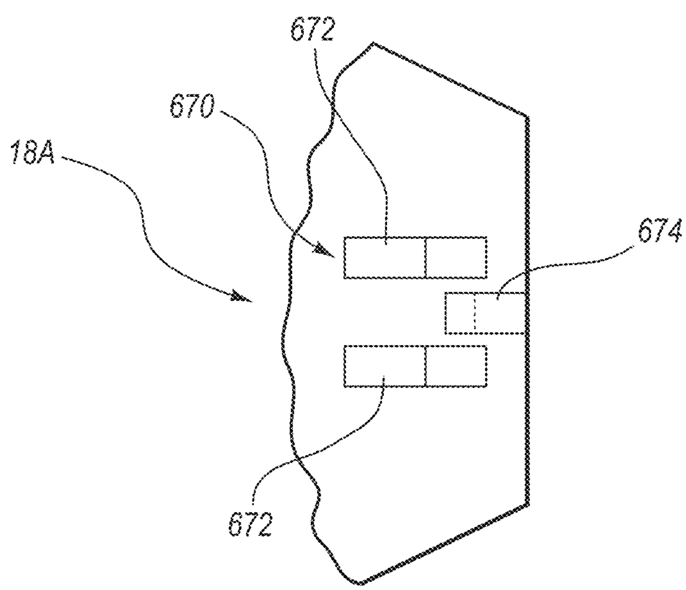
Figure 11D:
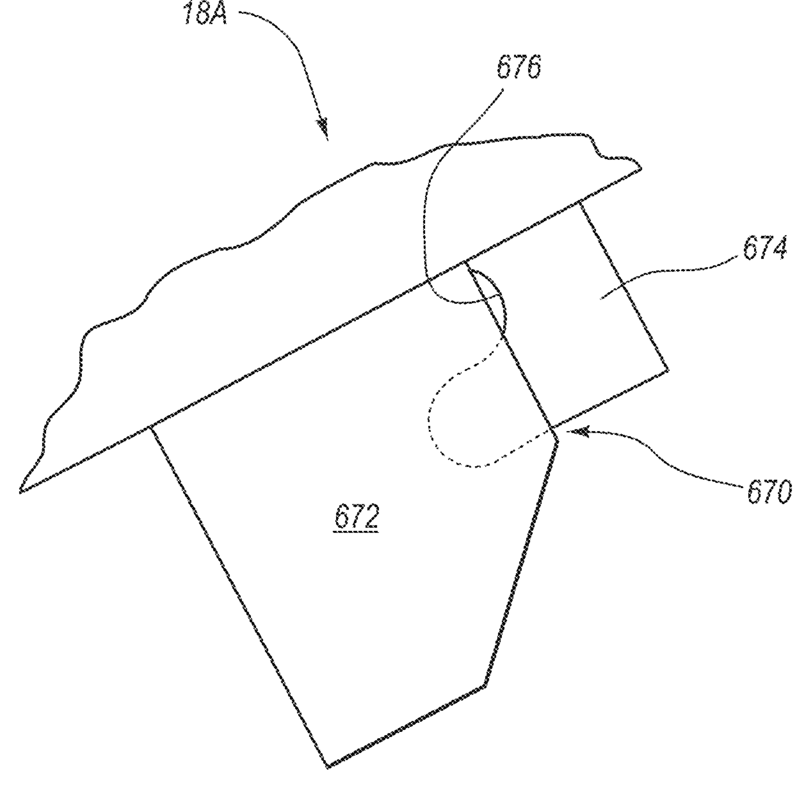

FIGS. 11A-11D depict one possible connector 670 for the probe head portion 18A for engaging a needle guide, according to one embodiment. In particular, the connector 670 includes two outer fins 672 in between which an inner fin 674 is positioned. As best seen in FIG. 11D, a recess 676 is included on the inner fin 674, and the outer fins 672, the inner fin 674, or all the fins include a resilient material so as to enable deformation thereof so as to facilitate insertion into the recess of a connector portion of the needle guide, such as the connector 456 of the needle guide 450 described in the embodiment associated with FIGS. 7A-8F, for example. In one embodiment, only the inner fin is resilient, while the outer fins are substantially rigid. It should therefore be appreciated that the manner of attachment between the needle guide and the probe can include any one of a number of possible designs. Also, it is appreciated that the needle channel can be defined in any one of a number of ways, in addition to the lips explicitly shown and described herein.

Figure 12:
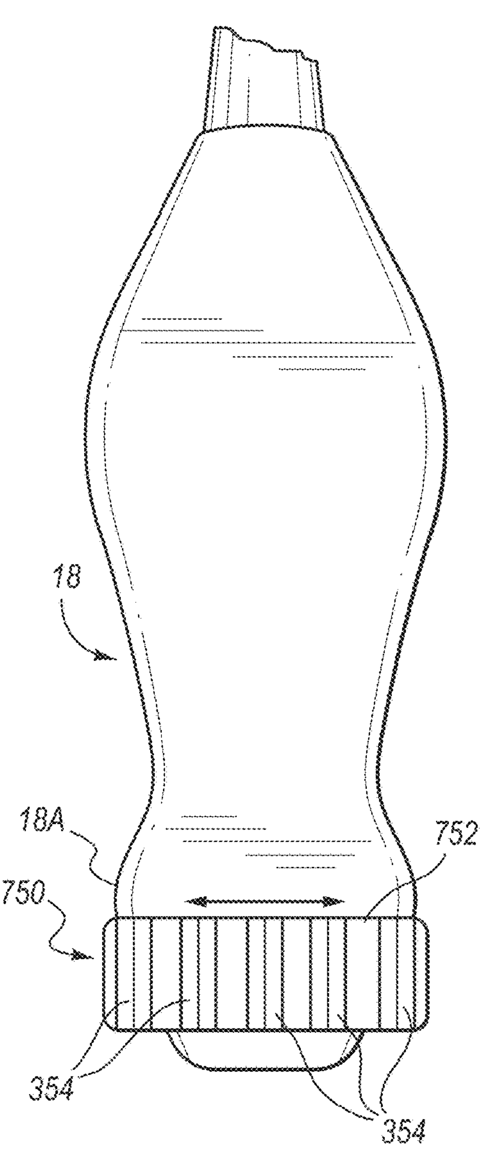
FIG. 12 is a top view of an adjustable needle guide system according to one another embodiment.
Figure 13:
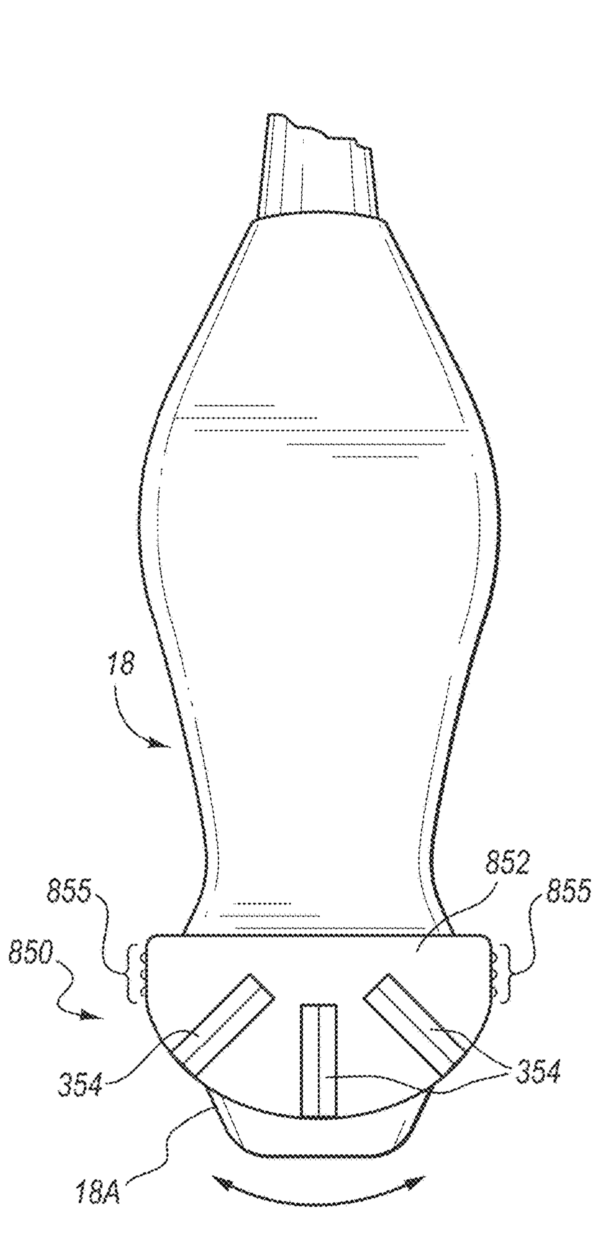
FIG. 13 is a top view of an adjustable needle guide system according to yet another embodiment.

FIGS. 12 and 13 depict yet other needle guide embodiments. In FIG. 12, a linear needle guide 750 is shown, including a top surface 752 on which are disposed a plurality of needle channels 354 that are each aligned to define differing needle insertion angles. A particular needle channel can be selected for use by laterally sliding the needle guide 750 as shown in FIG. 12. In FIG. 13, a semi-circular needle guide 850 is shown, including a top surface 852 on which a plurality of needle channels 354 are disposed in a fan pattern, each needle channel defining a different needle insertion angle. Finger grips 855 can be included on the body of the needle guide 850 to assist with movement of thereof to position a desired needle channel for use. These embodiments are therefore illustrative of the many different needle guide configurations possible.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An ultrasound probe system, comprising:
- an ultrasound probe comprising:
  - a head portion having a front surface;
  - a body portion having an engagement feature configured to engage with a first flexible extension of a first needle guide; and
  - a front guide connector attached to the front surface of the head portion, the front guide connector comprising:
    - an elongated protrusion defining a first side surface, a second side surface, and a top mounting surface;
    - a first stability extension extending from the first side surface; and
    - a second stability extension extending from the second side surface, the first stability extension and the second stability extension disposed along an axis orthogonal to a longitudinal axis of the elongated protrusion; and
- one or more needle guides designed for separate attachment to the front guide connector, the one or more needle guides including the first needle guide, and each of the one or more needle guides comprising:
  - an elongated cavity to receive the elongated protrusion;
  - a first side channel in communication with the elongated cavity designed to receive the first stability extension;
  - a second side channel in communication with the elongated cavity designed to receive the second stability extension;
  - a top surface including a first ridge and a second ridge together defining a needle channel in a central portion of the top surface, the needle channel having a longitudinal axis forming an angle with a longitudinal axis of the ultrasound probe; and
  - a flexible extension that is configured to engage with the engagement feature of the body portion of the ultrasound probe.

2. The ultrasound probe system according to claim 1, wherein the one or more needle guides comprises the first needle guide and a second needle guide, wherein the longitudinal axis of the needle channel of the first needle guide forms a first angle with the longitudinal axis of the ultrasound probe, and wherein the longitudinal axis of the needle channel of the second needle guide forms a second angle different from the first angle with the longitudinal axis of the ultrasound probe.

3. The ultrasound probe system according to claim 2, wherein the one or more needle guides comprises a third needle guide, wherein the longitudinal axis of the needle channel of the third needle guide forms a third angle different from the first angle and the second angle with the longitudinal axis of the ultrasound probe.

4. The ultrasound probe system according to claim 1, wherein the one or more needle guides comprises the first needle guide and a second needle guide, wherein the needle channel of the first needle guide has a first diameter, and wherein the needle channel of the second needle guide has a second diameter different from the first diameter.

5. The ultrasound probe system according to claim 4, wherein the one or more needle guides comprises a third needle guide, wherein the needle channel of the third needle guide has a third diameter different from the first diameter and the second diameter.

6. The ultrasound probe system according to claim 1, wherein a distal end of the elongated protrusion defines an overhang, the elongated cavity designed to receive the overhang.

7. The ultrasound probe system according to claim 1, wherein the first side surface of the elongated protrusion includes a first projection, wherein the second side surface of the elongated protrusion includes a second projection, and wherein each of the one or more needle guides includes a first depression and a second depression designed to receive, respectively, the first projection and the second projection.

8. The ultrasound probe system according to claim 1, further comprising a side guide connector attached to a side surface of the head portion, the side guide connector having dimensions matching the front guide connector, wherein the one or more needle guides are designed for separate attachment to the side guide connector.

9. The ultrasound probe system according to claim 1, wherein each of the one or more needle guides includes identifying indicia.

10. The ultrasound probe system according to claim 9, wherein the identifying indicia includes an optimal needle gauge for insertion through the needle channel.

11. The ultrasound probe system according to claim 9, wherein the identifying indicia includes a targeted insertion depth of a needle inserted through the needle channel based on the angle.

12. The ultrasound probe system according to claim 9, wherein the identifying indicia is presented on a distal front face of each of the one or more needle guides.

13. The ultrasound probe system according to claim 1, wherein the elongated cavity of each of the one or more needle guides is closed at a distal end and open at a proximal end.

14. The ultrasound probe system according to claim 13, wherein a distal end of each of the one or more needle guides includes an arcuate surface on a distal front face.

15. The ultrasound probe system according to claim 1, wherein engagement between the engagement feature and the flexible extension of each of the one or more needle guides defines a needle insertion angle.

16. The ultrasound probe system according to claim 1, wherein the engagement feature is a receiver array comprised of one or more bars.

17. The ultrasound probe system according to claim 16, wherein the flexible extension of each of the one or more needle guides includes a hook at a proximal end configured to engage with the one or more bars of the engagement feature.

18. The ultrasound probe system according to claim 1, wherein the engagement feature is a receiver array comprised of one or more slots.

19. The ultrasound probe system according to claim 18, wherein the flexible extension of each of the one or more needle guides is configured to engage with the one or more slots of the engagement feature.

* * * * *